(12) United States Patent
Berger

(10) Patent No.: US 9,023,917 B2
(45) Date of Patent: May 5, 2015

(54) COMPOSITIONS FOR ENDODONTIC INSTRUMENTS

(75) Inventor: Todd Berger, Owasso, OK (US)

(73) Assignee: DENTSPLY International Inc., York, PA (US)

( * ) Notice: Subject to any disclaimer, the term of this patent is extended or adjusted under 35 U.S.C. 154(b) by 0 days.

(21) Appl. No.: 13/045,744

(22) Filed: Mar. 11, 2011

(65) Prior Publication Data

US 2011/0230591 A1 Sep. 22, 2011

Related U.S. Application Data

(60) Provisional application No. 61/314,255, filed on Mar. 16, 2010.

(51) Int. Cl.
- *C08L 7/00* (2006.01)
- *A61C 5/04* (2006.01)
- *C08F 136/08* (2006.01)
- *A61K 6/00* (2006.01)

(52) U.S. Cl.
CPC ............... *A61C 5/04* (2013.01); *A61K 6/0088* (2013.01); *A61K 6/0091* (2013.01)

(58) Field of Classification Search
USPC .............................................. 433/224, 228.1
See application file for complete search history.

(56) References Cited

U.S. PATENT DOCUMENTS

| | | | | |
|---|---|---|---|---|
| 4,483,679 A * | 11/1984 | Fujisawa et al. | ........... | 433/228.1 |
| 4,544,359 A * | 10/1985 | Waknine | .......... | 522/14 |
| 4,547,531 A * | 10/1985 | Waknine | ....... | 523/116 |
| 4,632,977 A * | 12/1986 | Riazi | ............ | 528/481 |
| 4,740,245 A * | 4/1988 | Futami et al. | ......... | 106/35 |
| 4,758,156 A * | 7/1988 | Johnson | ............ | 433/81 |
| 4,766,200 A * | 8/1988 | Riazi | ............ | 528/502 F |
| 4,882,407 A * | 11/1989 | Riazi | ........... | 526/340.2 |
| 4,894,011 A | 1/1990 | Johnson | | |
| 4,966,952 A * | 10/1990 | Riaza | ......... | 526/340.2 |
| 5,118,297 A | 6/1992 | Johnson | | |
| 5,215,461 A * | 6/1993 | Riazi | ............ | 433/224 |
| 5,833,457 A | 11/1998 | Johnson | | |
| 6,353,041 B1 * | 3/2002 | Qian | ........... | 523/116 |
| 6,428,319 B1 * | 8/2002 | Lopez et al. | ......... | 433/224 |
| 6,439,890 B1 * | 8/2002 | Karmaker et al. | ........... | 433/220 |
| 6,447,297 B1 * | 9/2002 | Lopez et al. | ......... | 433/224 |
| 6,472,454 B1 * | 10/2002 | Qian | ........... | 523/116 |
| 6,500,004 B2 * | 12/2002 | Jensen et al. | ............ | 433/228.1 |
| 6,652,282 B2 * | 11/2003 | Jensen et al. | ............ | 433/228.1 |
| 6,809,137 B2 * | 10/2004 | Matsuo et al. | ........... | 524/282 |
| 6,811,400 B2 * | 11/2004 | Jensen et al. | ............ | 433/224 |
| 6,986,662 B2 * | 1/2006 | Haschke | ............ | 433/228.1 |
| 7,125,254 B2 * | 10/2006 | Calvert | ............ | 433/224 |
| 7,168,952 B2 | 1/2007 | Karmaker et al. | | |
| 7,252,508 B2 * | 8/2007 | Karmaker et al. | ............ | 433/224 |
| 7,261,563 B2 * | 8/2007 | Haschke | ............ | 433/224 |
| 7,384,576 B1 * | 6/2008 | Jungermann et al. | ........ | 252/478 |
| 7,553,912 B2 * | 6/2009 | Ikuta et al. | ......... | 525/343 |
| 7,838,573 B2 | 11/2010 | Primus et al. | | |

(Continued)

OTHER PUBLICATIONS

Inorganic Pharmaceutical Chemistry, Nuclear Chemistry, Oct. 2007, pp. 4-14 to 4-15, Nirali Prakashan.*

*Primary Examiner* — James J Seidleck
*Assistant Examiner* — Peter A Salamon
(74) *Attorney, Agent, or Firm* — David A. Zdurne; Douglas J. Hura; Leana Levin

(57) ABSTRACT

A carrier composition for filling a tooth root canal, comprising a cross-linkable material.

20 Claims, 4 Drawing Sheets

(56) References Cited

U.S. PATENT DOCUMENTS

| | | | |
|---|---|---|---|
| 7,850,453 B2* | 12/2010 | Jodaikin et al. | 433/215 |
| 8,298,664 B2* | 10/2012 | Jia | 428/357 |
| 2003/0124483 A1* | 7/2003 | Jia et al. | 433/81 |
| 2003/0134933 A1* | 7/2003 | Jin et al. | 523/115 |
| 2003/0165792 A1* | 9/2003 | Jodaikin et al. | 433/80 |
| 2003/0194682 A1* | 10/2003 | Jensen et al. | 433/224 |
| 2003/0199605 A1* | 10/2003 | Fischer | 523/116 |
| 2004/0115589 A1* | 6/2004 | Karmaker et al. | 433/81 |
| 2004/0202985 A1* | 10/2004 | Karmaker et al. | 433/220 |
| 2004/0209229 A1* | 10/2004 | Jensen et al. | 433/224 |
| 2004/0248067 A1* | 12/2004 | Lopez et al. | 433/220 |
| 2004/0265783 A1* | 12/2004 | Karmaker et al. | 433/220 |
| 2005/0003328 A1* | 1/2005 | Karmaker et al. | 433/220 |
| 2005/0011885 A1* | 1/2005 | Seghatol et al. | 219/679 |
| 2005/0066854 A1* | 3/2005 | Jia | 106/35 |
| 2005/0069836 A1* | 3/2005 | Jia et al. | 433/81 |
| 2005/0196726 A1* | 9/2005 | Fischer | 433/224 |
| 2006/0149000 A1* | 7/2006 | Ikuta et al. | 525/343 |
| 2007/0131139 A1* | 6/2007 | Jia et al. | 106/35 |
| 2007/0148616 A1* | 6/2007 | Jia et al. | 433/81 |
| 2007/0184405 A1* | 8/2007 | Jia et al. | 433/81 |
| 2008/0020353 A1* | 1/2008 | Jia | 433/220 |
| 2008/0108009 A1* | 5/2008 | Kert | 433/29 |
| 2008/0108015 A1* | 5/2008 | Karmaker et al. | 433/202.1 |
| 2008/0190322 A1* | 8/2008 | Chen et al. | 106/218 |
| 2008/0241799 A1* | 10/2008 | Tuttle et al. | 433/224 |
| 2008/0250974 A1* | 10/2008 | Jia | 106/35 |
| 2008/0286723 A1* | 11/2008 | Tuttle et al. | 433/224 |
| 2009/0042161 A1* | 2/2009 | Jodaikin et al. | 433/80 |
| 2009/0047634 A1* | 2/2009 | Calvert | 433/224 |
| 2009/0326114 A1* | 12/2009 | Grothe et al. | 524/148 |
| 2010/0015437 A1* | 1/2010 | Grothe et al. | 428/329 |

* cited by examiner

US 9,023,917 B2

COMPOSITIONS FOR ENDODONTIC INSTRUMENTS

FIELD OF THE INVENTION

The present invention is directed to a dental instrument, and specifically to an improved composition for endodontic instruments useful for filling root canals.

BACKGROUND OF THE INVENTION

Current methods of obturating (filling) an extirpated (stripped) root canal commonly involve packing a root canal with a thermoplastic material, such as gutta percha (e.g., trans 1-4 polyisoprene, Vectra™ or polysulfone), so that the root canal space is filled with the thermoplastic material. Preferably, the space is filled with the thermoplastic material forming a seal which prevents leakage between the root canal and the surrounding tissue.

It has been found that a satisfactory seal can be formed by softening the thermoplastic material by heating it prior to inserting it into the root canal. Normally, the gutta percha is applied to a carrier prior to insertion into the root canal in order to facilitate insertion. Carriers pre-coated with gutta percha are known, as shown by U.S. Pat. No. 4,758,156 issued on Jul. 19, 1988 to the inventor of the present invention and which is incorporated herein by reference. However, carriers pre-coated with gutta percha are expensive to purchase, and a less expensive means is desired for applying gutta percha to a carrier.

Although traditional thermoplastic compositions may be utilized in obturation carriers (e.g., Thermafil® Plus by Dentsply International, Inc, Soft-Core® by Axis Dental) that are generally effective in treating root canals, it would be desirable to have a carrier formed of a cross-linked composition. Thermoplastic materials, which are stable during high temperatures, must be crystalline and very hard. As such, a rotating file cannot penetrate the thermoplastic materials, and instead simply slides to one side of the carrier. This makes re-treating root canals somewhat difficult and certainly different than other obturation techniques like cold lateral and warm compaction.

By providing a carrier formed of a cross-linked material such as a thermoset material like rubber (e.g., gutta percha), retreatment of a root canal may be simplified. Ideally, the improved cross-linked carrier composition would have a desirable stiffness while generally being capable of maintaining its shape after the application of heat (e.g., during retreatment of a tooth). The present invention provides such improved carrier compositions having a cross-linked network and the desirable properties associated therewith.

SUMMARY OF THE INVENTION

The present invention seeks to improve upon prior obturation systems and particularly the filling a tooth root canal by providing an improved carrier composition having a cross-linkable material.

In another aspect, the present invention contemplates a carrier composition including about 1% to about 70% a thermoset material; about 0.1% to about 30% a curing agent; and about 0.05% to about 50% a filler.

In another aspect, the present invention contemplates a carrier composition including cis 1-4, polyisoprene; and a curing agent.

In yet another aspect, any of the aspects of the present invention may be further characterized by one or any combination of the following features: the cross-linkable material is a thermoset material; the cross-linkable material includes cis 1-4, polyisoprene; the cross-linkable material is present in an amount of about 1% to about 70% by wt of the carrier composition; the cross-linkable material is present in an amount of about 10% to about 40% by wt of the carrier composition; further comprising a curing agent; further comprising a coagent; the curing agent is present in an amount of about 0.1% to about 30% by wt of the carrier composition and the coagent is present in an amount of about 0.01% to about 30% by weight the carrier composition; further comprising an elastomer; the elastomer is present in an amount of about 0.1% to about 50% by wt of the carrier composition; the cross-linkable material to the elastomer is present in a ratio ranging from about 10:1 to about 1:1; the thermoset material includes cis 1-4, polyisoprene; the coagent is present in an amount of about 0.01% to about 30% by weight the carrier composition; the thermoset material to the elastomer is present in a ratio ranging from about 10:1 to about 1:1; further comprising a coagent, a radiopaque component, and a filler including at least one of reinforcing fillers and reinforcing fibers; or any combination thereof.

It should be appreciated that the above referenced aspects and examples are non-limiting as others exist with the present invention, as shown and described herein. For example, any of the above mentioned aspects or features of the invention may be combined to form other unique configurations, as described herein, demonstrated in the drawings, or otherwise.

DETAILED DESCRIPTION OF THE INVENTION

Figure 1:
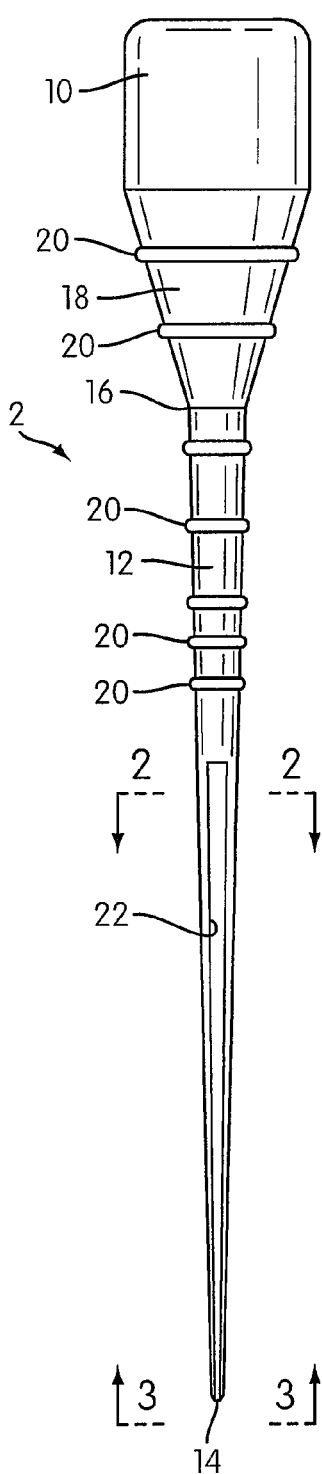
FIG. 1 is an elevational enlarged view of an endodontic obturator formed of the improved carrier composition of this invention.

Referring to the drawings and first to FIG. 1, an enlarged elevational view of an embodiment of the improved endodontic obturator is shown. The obturator includes a carrier body 2 formed of a cross-linked (e.g., thermoset) carrier material (e.g., carrier composition) of the present invention. The carrier body 2 includes a handle portion 10 and a shaft portion 12. In one embodiment, the handle portion 10 and the shaft portion 12 may be integrally formed of the carrier material. In another embodiment, the handle portion 10 and the shaft portion 12 may be separately formed and then attached thereafter. It is contemplated that when separately formed, the handle portion 10 may be formed of a material different than the material of the shaft portion 12. Preferably, the handle portion 10 and the shaft portion 12 are both formed of the cross-linked carrier material. However, it is further contemplated that in another embodiment, only the shaft portion 12 is formed of the cross-linked carrier material.

In one embodiment, the proximal handle portion 10 may be dimensioned to be manipulated between the thumb and forefinger of the user. Integrally extending from handle portion 10 may be a shaft portion 12 that terminates in a distal end 14. Shaft 12 may be tapered and has an external surface adapted to receive an optional endodontic filler material 26 (e.g., coating), such as gutta percha, thereon. Preferably, shaft portion 12 tapers from the maximum diameter at junction 16 where the shaft meets a conical portion 18 of handle 10, the shaft tapering from a maximum diameter at junction 16 to a minimum diameter at distal end 14.

In one specific embodiment, the carrier body may be supplied directly by a manufacturer with the filler material formed thereon, the material being subject to being heated in a flame or in an oven to soften the filler material before it is inserted into a root canal. Furthermore, the carrier body may include a sliding stopper or washer on the obturator body shaft.

In another embodiment, integrally formed on shaft 18 may be spaced apart length indicators 20 that are, as explained in U.S. Pat. No. 5,118,297, useful for indicating the distance that the shaft proximal end 14 has penetrated into a root canal so that the practitioner can, after the canal is filled with a filler material, insert the obturator and know that the distal end has penetrated to the depth as indicated by an indicator 20. Handle portion 18 may include depth indicators that are useful when the obturator is employed in a tooth having an unusually long root canal.

It is contemplated that junction 16 may be an external indication only of change in the shape of the tapered surface of shaft 12 and handle conical portion 18 and may not indicate a separation in the overall integral obturator.

Figure 2:
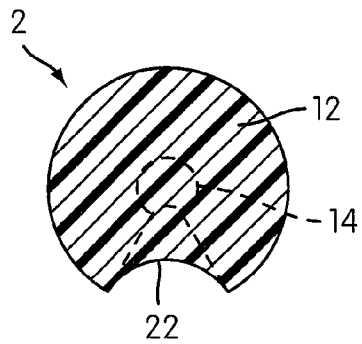
FIG. 2 is a greatly enlarged cross-sectional view as taken along the line 2-2 of FIG. 1 showing one configuration of a groove as provided in the external surface of the shaft portion of a carrier body.
Figure 4:
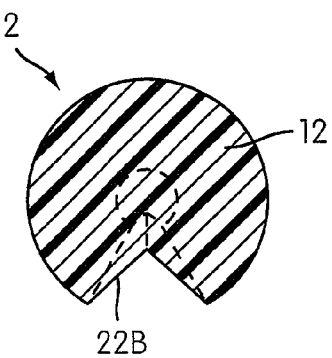
FIG. 4 is a cross-sectional view as shown in FIG. 2 but showing an alternate design of the groove formed in the external surface of the shaft portion of the carrier body.

FIG. 2 shows a cross-section of the obturator shaft 12 and an optional groove 22. In this figure, groove 22 may be generally arcuate; however the cross-sectional shape of the groove can vary. For instance, FIG. 4 is an alternate embodiment wherein groove 22B has an angular cross-sectional configuration. The angle forming the walls of the groove can vary considerably from an acute to an obtuse angle. Not only can the cross-sectional shape of groove 22 vary but the depth can vary considerably.

When included, an advantage of the provision of the optional groove 22 may be that it allows for the escape of excess filler material (e.g., coating) as the obturator (e.g., carrier body and filler material coated thereon) is inserted into a root canal having filler material therein. A function of the obturator may be to compact filler material in a root canal to eliminate, as much as possible, or substantially reduce any voids and to cause the filler material to flow into lateral fissures that frequently characterize root canals. When the obturator is inserted into a root canal having filler material therein, the obturator should be positioned at its full depth into the canal with distal end 14 as close as practically possible to the root canal apex and therefore, any excess accumulation of filler material in the root canal can, by hydraulic action, interfere with positioning the obturator in the root canal in a tooth in some instances. With the provision of groove 22 any excess filler material can flow to the tooth surface and hydraulically resistance to positioning the obturator shaft portion in the root canal is alleviated.

The provision of the optional groove 22 is generally formed in the external surface of the obturator shaft portion 12. Groove 22 may extend from an upper portion of shaft 12 to distal end 14. In the embodiment of FIG. 1 the groove extends completely to the end of shaft portion 14, though not required.

Figure 3:
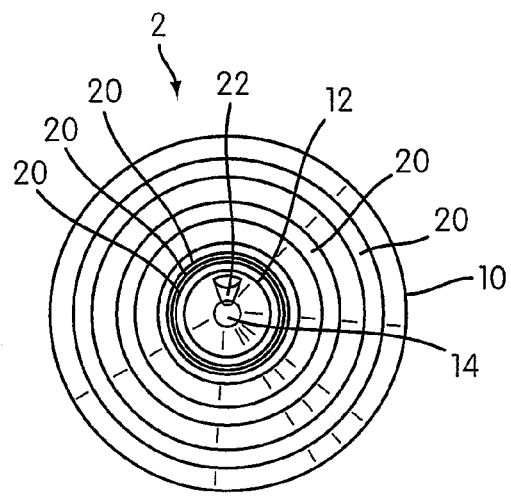
FIG. 3 is an enlarged end view as taken along the line 3-3 of FIG. 1.
Figure 5:
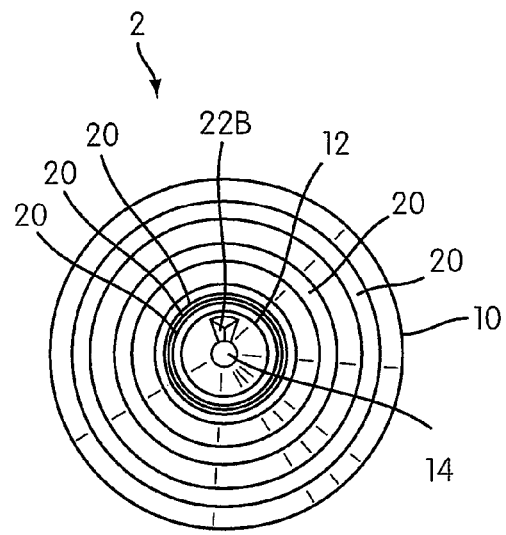
FIG. 5 is a view as shown in FIG. 3 but showing the appearance of a carrier body as seen from the distal end when a groove having straight sidewalls as shown in FIG. 4 is employed.

FIG. 3 is an end view of the obturator showing the groove 22 extending to distal end 14. FIG. 5 shows an end view of an obturator having an angular groove 22B as shown in FIG. 4.

Figure 6:
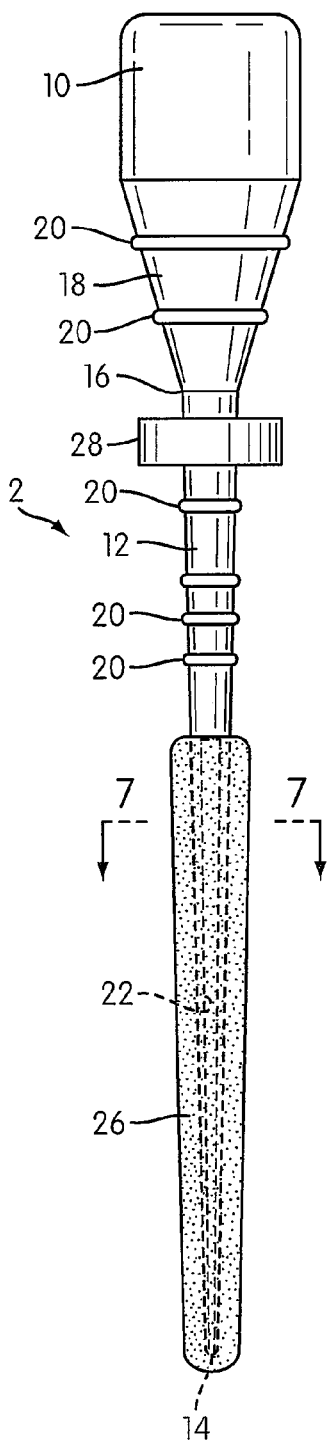
FIG. 6 is an elevational view of a carrier body, such as one shown in FIG. 1, but including filler coating material adhered to the shaft portion.
Figure 7:
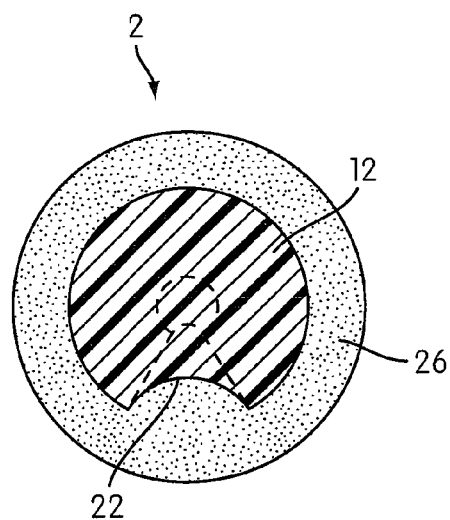
FIG. 7 is an enlarged cross-sectional view as taken along the line 7-7 of FIG. 6 showing the carrier body in cross-section having a groove with an arcuate cross-sectional configuration and showing the filler material as formed on the carrier shaft portion.

An important advancement of the state of endodontics has been the commercial availability of obturators having filler material formed thereon. FIGS. 6 and 7 show the obturator of FIG. 1 having filler material 26 (e.g., coating) formed thereon (e.g., generally surrounding a portion of the carrier 2 such as shaft portion 12). Filler material 26 may typically include gutta percha but other compounds which have the desirable characteristic to function as a root canal filler are possible. The typical commercially available obturator has filler material 26 thereon which at ambient temperature is relatively rigid. Filler material 26 can be heated either over an open flame or in an oven to a temperature at which it become semi-molten before the obturator having the filler material thereon is inserted into a root canal.

FIG. 6 shows an elastomeric washer 28 that can be used for assistance in compacting a filler material 26 into a root canal, as has been explained in the previously issued patents referred to herein.

Figure 8:
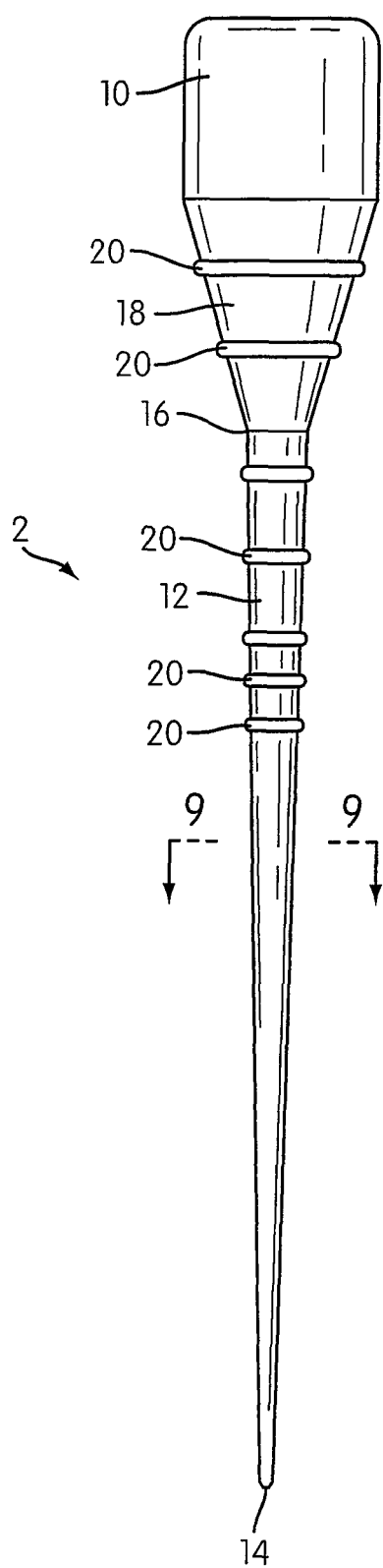
FIG. 8 is an elevational enlarged view of another embodiment of the endodontic obturator formed of the improved carrier composition of this invention.
Figure 9:
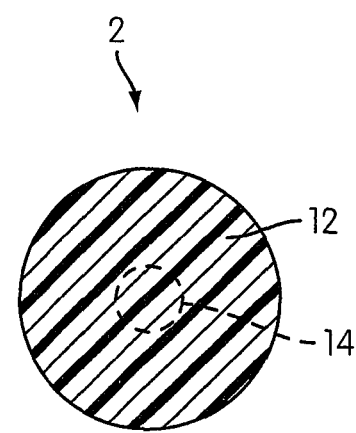
FIG. 9 is a greatly enlarged cross-sectional view as taken along the line 9-9 of FIG. 8 showing the external surface of the shaft portion of a carrier body.
Figure 10:
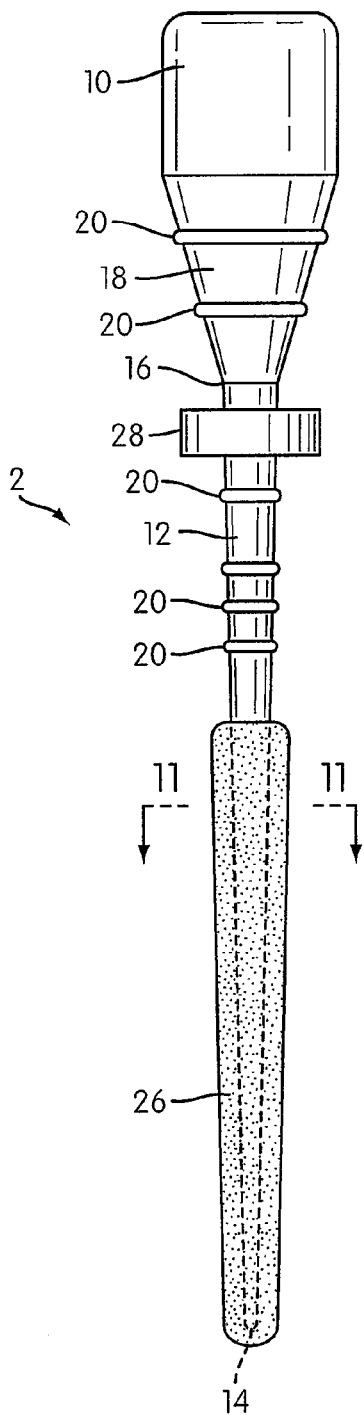
FIG. 10 is an elevational view of a carrier body, such as one shown in FIG. 8, but including filler coating material adhered to the shaft portion.
Figure 11:
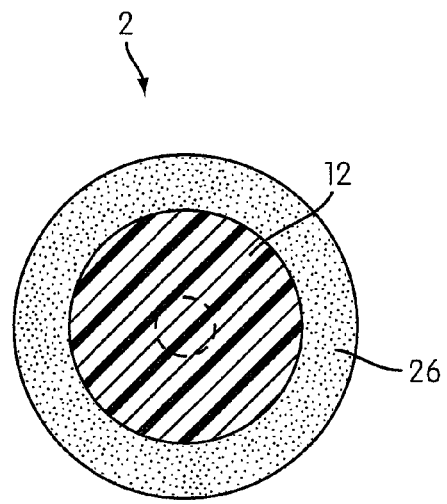
FIG. 11 is an enlarged cross-sectional view as taken along the line 11-11 of FIG. 10 showing the carrier body in cross-section showing the filler coating material as formed on the carrier shaft portion.

FIGS. 8-9 show another embodiment of the present invention. These figures generally include similar corresponding features and respective numeric identifiers as in FIGS. 1-2, however without the optional groove. As shown in FIGS. 10-11, an optional filler material 26 is provided, which may be adhered to the shaft portion of the carrier body shown in FIGS. 8-9.

The obturator described to this point includes features generally disclosed in previously issued U.S. Pat. Nos. 4,894,011, 5,118,297, and 5,833,457, which are incorporated herein by reference for all purposes.

A significant and important improvement is the material utilized in forming the carrier body of the obturator. More particularly, the carrier body of the present invention may be formed of a chemically cross-linked material (e.g., a thermoset material). The thermoset material may be formed (e.g., molded) into a carrier body (e.g., handle portion and/or shaft portion) that when cooled, may substantially (e.g., permanently) hold its shape. Advantageously, upon application of heat the chemically cross-linked material will substantially or completely maintain its shape. Furthermore, thermoset materials (e.g., thermoset rubbers) may generally have rather poor tear properties thus making it easy to penetrate the carrier with a rotating file (e.g., during retreatment of a root canal).

The present invention provides a carrier composition with an improved physical property directed to the stiffness and/or storage modulus over temperature, which may be measured using Dynamic Mechanical Thermal Analysis (DMTA). It is appreciated that the stiffness may be controlled by the addition of one or more of the components discussed herein.

The carrier composition includes a cross-linkable (e.g., thermoset) material (e.g., first rubber and/or plastic). Examples of cross-linkable material include, but are not limited to, alkyds, epoxies, phenolics (e.g., Bakelite), polyimides, formaldehyde resins (e.g., urea formaldehyde or melamine formaldehyde), polyester thermosets, unsaturated polyesters, polyurethane, bis-maleimides (BMI), silicone, the like, or any combinations thereof. The cross-linkable material may be present in an amount of at least about 1%, and preferably at least about 5% by wt of the carrier composition. Furthermore, the cross-linkable material may be present in an amount of less than about 70%, and preferably less than about 45% by wt of the carrier composition. For example, the cross-linkable material may be present in a range from about 1% to about 70%, and preferably from about 5% to about 45% (e.g., about 10% to about 25%) by wt of the carrier composition.

In one preferred embodiment the cross-linkable material may include cis 1-4, polyisoprene. It is appreciated that the cis 1,4, polyisoprene has a carbon-carbon double bond in its backbone thereby allowing for the curing agent and/or coagent to open this double bond and create a solid 3 dimensional covalently bonded network. In doing so, the soft gummy polymer network may be converted (e.g., cross-linked) into a solid over all temperatures until the material chemically decomposes.

The cross-linkable material (e.g., cis 1-4, polyisoprene) may be present instead of or in addition to the traditional thermoplastic material such as gutta percha (trans 1-4, polyisoprene). However, it may be desirable that the carrier composition is free of any thermoplastic material, though not required. In one specific example, cis 1-4, polyisoprene may be present instead of trans 1-4, polyisoprene so that the carrier composition is free of trans 1-4, polyisoprene. A preferred cis 1-4, polyisoprene is NATSYN® 2200 and/or 2200 sold by GOODYEAR CHEMICAL of Akron Ohio. Another preferred cis 1-4, polyisoprene is Nipol IR 2200 sold by Zeon Chemicals of Louisville, Ky. Other cis 1-4, polyisoprene are contemplated as well as using one of the many forms of trans 1,4-polyisoprene.

In another embodiment, it has been found that adding a second elastomer (e.g. rubber) may improve processing (e.g., increased blending, increased flow properties, or otherwise). When included, desirable elastomers may include, but are not limited to, ethylene propylene diene monomer (EPDM), Styrene-Butadiene-Rubber (SBR), Acrylonitrile-butadiene rubber (NBR), Hydrogenated Nitrile Hydrogenated Acrylonitrile-butadiene rubber (HNBR), Chloroprene rubber (CR), Silicone rubber (VMQ), Polyacrylate rubber (ACM), Ethylene Acrylic rubber (AEM), Polyurethane such as Polyester urethane/Polyether urethane (AU/EU, respectively), Natural rubber (NR), the like or otherwise, and combinations thereof. For example, when included a ratio to cross-linkable material (e.g., cis 1-4 polyisoprene) to second elastomer (e.g., EPDM) may range from about 10:1 to about 1:1, and preferably from about 5:1 to about 2:1 (e.g., 3:1). The elastomer may be present in an amount of at least about 0.1%, and preferably at least about 1% by wt of the carrier composition. Furthermore, the elastomer may be present in an amount of less than about 50%, and preferably less than about 25% by wt of the carrier composition. For example, the elastomer may be present in a range from about 0.1% to about 50%, and preferably from about 1% to about 25% (e.g., about 3% to about 15%) by wt of the carrier composition. A preferred rubber is an EPDM rubber with the commercial name Vistalon™ sold by ExxonMobil Chemical of Houston, Tex.

The carrier composition may include a, curing agent (e.g., cross-linker), coagent, or a combination of both. It is appreciated that the curing agent and/or coagent may be employed to chemically cross link cis 1-4, polyisoprene. Examples of a cross-linker may include, but are not limited to, fine sulfur (e.g., sulfur vulcanization of polyisoprene accelerated by benzothiazole derivatives such as the reaction of 2-bisbenzothiazole-2,2'-disulfide with sulfur and ZnO in polyisoprene), peroxide (e.g., 2,5-dimethyl-2,5-di(t-butylperoxy) hexane), zinc diacrylate (e.g., Saret® SR633), polybutadiene resin (e.g., Ricon 153), the like or otherwise, or combinations thereof. The curing agent (e.g., cross-linker) may be present in an amount of at least about 0.1%, and preferably at least about 5% by wt of the carrier composition. Furthermore, the curing agent may be present in an amount of less than about 70%, and preferably less than about 45% by wt of the carrier composition. For example, the curing agent may be present in a range from about 0.1% to about 70%, and preferably from about 5% to about 45% (e.g., about 10% to about 25%) by wt of the carrier composition. A preferred cross-linker is 2,5-dimethyl-2,5-di(t-butylperoxy) hexane having the commercial name Varox® DBPH sold by R. T. Vanderbilt Company of Norwalk, Conn.

Examples of a coagent may include, but are not limited to, mercaptobenzathiazole (e.g., 2-mercaptobenzathiazole), peroxide (e.g., 2,5-dimethyl-2,5-di(t-butylperoxy) hexane), acyrlates, the like or otherwise, or combinations thereof. Acrylate coagents may include methacrylates (e.g., trimethacrylates), methylmethacrylates, or otherwise, and combinations thereof. The coagent may be present in an amount of at least about 0.01%, and preferably at least about 0.5% by wt of the carrier composition. Furthermore, the coagent may be present in an amount of less than about 40%, and preferably less than about 25% by wt of the carrier composition. For example, the coagent may be present in a range from about 0.01% to about 40%, and preferably from about 0.5% to about 25% (e.g., about 1% to about 10%) by wt of the carrier composition. A preferred coagent is a trimethylolpropane trimethacrylate having the commercial name SR350 sold by Sartomer of Exton, Pa.

It is appreciated that cross-linker/coagent combinations may include a 2,5-dimethyl-2,5-di(t-butylperoxy) hexane cross-linker and a trimethylolpropane trimethacrylate coagent, a fine sulfur cross-linker and a mercaptobenzathiazole coagent, a zinc diacrylate cross-linker and a 2,5-dimethyl-2,5-di(t-butylperoxy) hexane coagent, a polybutadiene resin cross-linker and a 2,5-dimethyl-2,5-di(t-butylperoxy) hexane coagent, and/or a 2,5-dimethyl-2,5-di(t-butylperoxy) hexane cross-linker and a trimethylolpropane trimethacrylate coagent. However, other cross-linker and/or coagents are contemplated as well as any combinations thereof.

The carrier composition of the present invention forms a new material that will be generally stiff. This stiffness results from a combination of cross linking, fillers, reinforcing fillers, nanotubes, fibers, and/or otherwise, or any combination thereof. The nano-technologies may include, but are not limited to nano particles, nano fibers as well as nano tubes as discussed herein. Furthermore, other nano technologies may be incorporated into the carrier composition to provide additional stiffness characteristics. It is appreciated that the fillers, reinforcing fillers, nanotubes, and/or fibers may generally add to the stiffness of the cured material without hindering the uncured material from flowing to fill the mold cavity during the production of the carrier (e.g., to improve processability).

The carrier composition may further include a filler such as zinc oxide, silica, titanium dioxide, iron oxides, silicon nitrides, glasses such as calcium, lead, lithium, cerium, tin, zirconium, strontium, barium, and aluminum-based glasses, borosilicate glasses, strontium borosilicate, barium silicate, lithium silicate, lithium alumina silicate, kaolin, quartz, and talc, Preferred fillers include generally fine particle sizes, however, not required. The filler may be present in an amount of at least about 0.001%, and preferably at least about 0.05% by wt of the carrier composition. Furthermore, the filler may be present in an amount of less than about 80%, and preferably less than about 50% by wt of the carrier composition. For example, filler may be present in a range from about 0.001% to about 80%, and preferably from about 0.05% to about 50% by wt of the carrier composition.

In one specific example, the filler may include zinc oxide (e.g., antimicrobial). When included, zinc oxide may be present in an amount of at least about 0.001%, and preferably at least about 0.05% by wt of the carrier composition. Furthermore, the zinc oxide may be present in an amount of less than about 50%, and preferably less than about 25% by wt of the carrier composition. For example, zinc oxide may be present in a range from about 0.001% to about 50%, and preferably from about 0.01% to about 25% (e.g., about 0.05% to about 10%) by wt of the carrier composition. A preferred zinc oxide filler is sold under the commercial name zinc oxide 35 from Akrochem Corporation of Akron Ohio.

The filler may include a reinforcing filler. It is believed that reinforcing fillers help improve physical and/or chemical bonding to the polymer, which may result in improved stiffening of the carrier compound once (fully) cross linked. The reinforcing filler may include precipitated silica, fumed silica, silane treated silica, carbon black particles, clay, the like or otherwise, or any combination thereof. The reinforcing filler may be present in an amount of at least about 0.01%, and preferably at least about 0.1% by wt of the carrier composition. Furthermore, the reinforcing filler may be present in an amount of less than about 60%, and preferably less than about 30% by wt of the carrier composition. For example, the reinforcing filler may be present in a range from about 0.01% to about 60%, and preferably from about 0.1% to about 30% (e.g., about 1% to about 15%) by wt of the carrier composition. A preferred reinforcing filler is a precipitated silica of the commercial name Hi-Sil 233 sold by PPG of Monroeville, Pa.

The filler may include filling fibers (e.g., carbon fibers, glass fibers, or otherwise, or any combination thereof). It is appreciated that typical filling fibers may have high length to width ratios (e.g., generally smaller than nano tubes and/or nano fibers). When included the filling fibers may include a fiber length of about 100 nm to about 2.0 mm, and preferably about 200 nm to about 500 nm (e.g., about 200 nm to about 300 nm). Filling fibers may provide additional stiffness to the carrier compound.

In one specific example, filling fibers may provide additional stiffness to the carrier compound in the flow direction during injection molding. Other forming processes may be employed such as calendaring the carrier material followed by compression molding. The filling fibers may be present in an amount of at least about 0.01%, and preferably at least about 0.1% by wt of the carrier composition. Furthermore, the filling fibers may be present in an amount of less than about 60%, and preferably less than about 30% by wt of the carrier composition. For example, the filling fibers may be present in a range from about 0.01% to about 60%, and preferably from about 0.1% to about 30% (e.g., about 1% to about 15%) by wt of the carrier composition. A preferred filling fiber is a glass fiber of the commercial name A200 Aramid fiber sold by PPG of Akron, Ohio.

The filler may include nano-technology as a stiffener such as nano-tubes, nano-particles, nano-fibers, or any combination thereof. The nano-technology may be carbon based or non carbon-based. It is appreciated that the nano-technology may include a length to width ratio of greater then about $10^3$, and preferably greater than $10^6$, which may provide the ability to be easily aligned into a flow field, thereby increasing the stiffness of injection molded part.

It is further appreciated that filler such as silane treated (coated) silica, carbon nano tubes (coated) fibers and/or otherwise may generally add to the stiffness of the cured material without hindering the uncured material from flowing to fill a mold cavity during the production of the carrier (improve processability).

The carrier composition may include one or more optional additives. The additives may include a radiopaque material, a stabilizer, an antimicrobial (e.g., Zinc Oxide), an anti-oxidant (e.g., 2,2 methylene-bis(4-methyl-6-tbutylphenol) such as Westco AO-2246), a plasticizer (e.g., Struktol® WB 222), an acid (e.g., stearic acid), a mold releasing agent such as a metal soap (e.g., zinc stearate), a wax (e.g., a paraffin wax such as No Check wax), softening agents, humectants, lubricants, the like or otherwise, or any combination thereof. The additive may be present in an amount of at least about 0.001%, and preferably at least about 0.01% by wt of the carrier composition. Furthermore, the additive may be present in an amount of less than about 50%, and preferably less than about 25% by wt of the carrier composition. For example, the additive may be present in a range from about 0.001% to about 50%, and preferably from about 0.01% to about 25% (e.g., about 0.05% to about 10%) by wt of the carrier composition.

Examples of a radiopaque material (e.g., radiopacifier) include, but are not limited to, bismuth oxide, barium sulfate, tungsten, tantalum oxide, cerium oxide tin oxide, zirconium oxide compounds and radiopaque glasses containing tantalum, barium and strontium, the like or otherwise, and combinations thereof. When included, the radiopacifier may have an average particle size of about 0.25 microns to about 10 microns, and preferably about 1.25 microns to about 2 microns (e.g., 1.40 microns to about 1.99 microns). In one example, the radiopacifier may be present having a mesh size from about 200 to about 500 (e.g., 270 and/or 325). The radiopaque material may be present in an amount of at least about 1%, and preferably at least about 10% by wt of the carrier composition. Furthermore, the radiopaque material may be present in an amount of less than about 75%, and preferably less than about 50% by wt of the carrier composition. For example, the radiopaque material may be present in a range from about 1% to about 75%, and preferably from about 10% to about 50% (e.g., about 25% to about 45%) by wt of the carrier composition. A preferred radiopacifier is tungsten 325 mesh c6 sold by Buffalo Tungsten of Depew, N.Y.

The carrier composition may include one or more pigments (e.g., colorants). A desirable colorant may produce a dark carrier to optionally be surrounded by a pink gutta percha material. Another desirable colorant may produce a pink carrier to be optionally surrounded by a pink gutta percha material. In one specific example, the exterior of the carrier may be coated with pink gutta percha and by matching this color the final obturated root canal would have a uniform appearance. However, in other embodiments the carrier compound may include various colorants where different sized carriers may be color coded to represent the different sizes. It is further appreciated that other colorants and/or colorant combination have been contemplated by the present invention. The colorant may be present in an amount of at least about 0.01%, and preferably at least about 0.05% by wt of the carrier composition. Furthermore, the colorant may be present in an amount of less than about 50%, and preferably less than about 35% by wt of the carrier composition. For example, the colorant may be present in a range from about 0.01% to about 50%, and preferably from about 0.05% to about 35% (e.g., about 0.1% to about 20%) by wt of the carrier composition. Desirable colorants may include Red MB, Yellow EPMB, Titanium dioxide, or otherwise, and any combinations thereof.

In one specific example of the present invention, the cross-linked carrier material may include the following composition:

| Component | Weight % |
| --- | --- |
| 1-4, Polyisoprene | 10 to 40 |
| Curing Agent | 0.1 to 30 |
| Curing Co agent | 0.01 to 30 |
| Zinc Oxide | 0 to 80 |
| Radiopacifier | 0 to 40 |
| Reinforcing Fillers | 0 to 50 |
| Carbon Nanotubes | 0 to 50 |
| Fibers | 0 to 50 |
| Colorant | 0 to 10 |

In another specific example of the present invention, the cross-linked carrier material may include the following composition:

| Component | Weight % |
| --- | --- |
| Cross-Linkable Material | 10 to 40 |
| Rubber | 0.5 to 15 |
| Curing Agent | 0.1 to 30 |
| Curing Co agent | 0.01 to 15 |
| Antimicrobial | 0.01 to 50 |
| Radiopacifier | 5.0 to 60 |
| Reinforcing Fillers | 0.5 to 30 |
| Fibers | 0.5 to 30 |
| Colorant | 0.01 to 25 |
| Anti Oxidant | 0 to 10 |
| Processing Aid | 0 to 10 |

Prototype Description—Physical Properties/Characteristics

In one preferred embodiment, the carrier composition may be compression molded for 7 minutes at 365° F. (185° C.) to form a resultant cross-linked carrier. The resultant cross-linked carrier may be defined by any one of the following characteristics: specific gravity from about 1.5 to about 3.0 (e.g., from about 1.8 to about 2.2); shrinkage of less than about 10%, preferably less than about 5% (e.g., from about 1% to about 3%); hardness (Shore D) of at least about 15, and preferably at least about 25 (e.g., about 40); tensile strength of at least about 500, and preferably at least about 1000 (e.g., about 1200) psi; elongation at break of at least about 0.5%, and preferably at least about 2%, or any combination thereof.

It will be further appreciated that functions or structures of a plurality of components or steps may be combined into a single component or step, or the functions or structures of one-step or component may be split among plural steps or components. The present invention contemplates all of these combinations. Unless stated otherwise, dimensions and geometries of the various structures depicted herein are not intended to be restrictive of the invention, and other dimensions or geometries are possible. In addition, while a feature of the present invention may have been described in the context of only one of the illustrated embodiments, such feature may be combined with one or more other features of other embodiments, for any given application. It will also be appreciated from the above that the fabrication of the unique structures herein and the operation thereof also constitute methods in accordance with the present invention. The present invention also encompasses intermediate and end products resulting from the practice of the methods herein. The use of "comprising" or "including" also contemplates embodiments that "consist essentially of" or "consist of" the recited feature.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes.

The invention claimed is:

1. A carrier composition for filling a tooth root canal, comprising
   about 1% to about 25% a thermoset material, the thermoset material being cis 1-4 polyisoprene;
   a curing agent;
   about 25% to about 45% a radiopacifier, the radiopacifier having an average particle size of about 1.25 microns to about 2 microns;
   about 0.05% to about 50% a filler; and
   about 0.5 to about 15% an elastomer;
   wherein cis 1-4 polyisoprene to the elastomer is present in a ratio ranging from about 10:1 to about 1:1.

2. The carrier composition of claim 1, further comprising a coagent.

3. The carrier composition of claim 2, wherein the curing agent is present in an amount of about 0.1% to about 30% by wt of the carrier composition and the coagent is present in an amount of about 0.01% to about 30% by weight the carrier composition.

4. A carrier composition for filling a tooth root canal, comprising:
   about 5% to about 45% cis-1-4 polyisoprene;
   about 0.1% to about 30% a curing agent;
   about 10% to about 50% a radiopacifier, the radiopacifier having an average particle size of about 1.25 microns to about 2 microns;
   about 0.5 to about 15% an elastomer; and
   about 1% to about 15% at least one of reinforcing fillers and reinforcing fibers;
   wherein the thermoset material to the elastomer is present in a ratio ranging from about 10:1 to about 1:1.

5. The carrier composition of claim 4, further comprising a coagent.

6. The carrier composition of claim 5, wherein the coagent is present in an amount of about 0.01% to about 30% by weight the carrier composition.

7. The carrier composition of claim 4, wherein the thermoset material to the elastomer is present in a ratio ranging from about 10:1 to about 1:1.

8. The carrier composition of claim 1, wherein the filler includes reinforcing fillers and reinforcing fibers, the reinforcing fillers being present in an amount from about 0.1% to about 30% by wt the carrier composition and being selected from the group consisting of precipitated silica, fumed silica, silane treated silica, carbon black particles, and clay, the reinforcing fibers being present in an amount from about 0.1% to about 30% by wt the carrier composition and having a fiber length of about 100 nm to about 2.0 mm.

9. The carrier composition of claim 4, wherein the reinforcing fillers are present in an amount of about 1% to about 15% and the reinforcing fibers are present in an amount of about 1% to about 15%.

10. The carrier composition of claim 9, further comprising a wax.

11. The carrier composition of claim 4, wherein the cis-1-4 polyisoprene is present in an amount of about 10% to about 25% by wt of the carrier composition.

12. The carrier composition of claim 1, wherein the filler includes about 1% to about 15% reinforcing fillers being selected from the group consisting of precipitated silica, fumed silica, silane treated silica, carbon black particles, and clay and about 1% to about 15% reinforcing fibers having a fiber length of about 100 nm to about 2.0 mm.

13. The carrier composition of claim 12, wherein the cis 1-4, polyisoprene is present in an amount of about 10% to about 25% by wt of the carrier composition.

14. The carrier composition of claim 1, wherein the elastomer is selected from the group consisting of ethylene propylene diene monomer (EPDM), Styrene-Butadiene-Rubber (SBR), Acrylonitrile-butadiene rubber (NBR), Hydrogenated Nitrile Hydrogenated Acrylonitrile-butadiene rubber (HNBR), Chloroprene rubber (CR), Silicone rubber (VMQ), Polyacrylate rubber (ACM), Ethylene Acrylic rubber (AEM), and Polyurethane.

15. The carrier composition of claim 1, wherein the radiopacifier is selected from the group consisting of bismuth oxide, barium sulfate, tungsten, tantalum oxide, cerium oxide tin oxide, and zirconium oxide.

16. The carrier composition of claim 1, wherein the radiopacifier is selected from the group consisting of bismuth oxide, tungsten, tantalum oxide, cerium oxide tin oxide, and zirconium oxide.

17. The carrier composition of claim 4, wherein the elastomer is selected from the group consisting of ethylene propylene diene monomer (EPDM), Styrene-Butadiene-Rubber (SBR), Acrylonitrile-butadiene rubber (NBR), Hydrogenated Nitrile Hydrogenated Acrylonitrile-butadiene rubber (HNBR), Chloroprene rubber (CR), Silicone rubber (VMQ), Polyacrylate rubber (ACM), Ethylene Acrylic rubber (AEM), and Polyurethane.

18. The carrier composition of claim 4, wherein the radiopacifier is selected from the group consisting of bismuth oxide, barium sulfate, tungsten, tantalum oxide, cerium oxide tin oxide, and zirconium oxide.

19. The carrier composition of claim 4, wherein the radiopacifier is selected from the group consisting of bismuth oxide, tungsten, tantalum oxide, cerium oxide tin oxide, and zirconium oxide.

20. The carrier composition of claim 4, wherein the reinforcing fillers are selected from the group consisting of precipitated silica, fumed silica, silane treated silica, carbon black particles, and clay and the reinforcing fibers have a fiber length of about 100 nm to about 2.0 mm.

* * * * *